(12) United States Patent
van Venrooij et al.

(10) Patent No.: US 10,588,710 B2
(45) Date of Patent: Mar. 17, 2020

(54) MEDICAL DEVICE ANCHORING

(71) Applicant: Medtronic, Inc., Minneapolis, MN (US)

(72) Inventors: Paulus C. van Venrooij, Hoensbroek (NL); Victor Duijsens, Grevenbicht (NL); Phillip C. Falkner, Minneapolis, MN (US); Franciscus Van Boekel, Boxtel (NL)

(73) Assignee: Medtronic, Inc., Minneapolis, MN (US)

( * ) Notice: Subject to any disclaimer, the term of this patent is extended or adjusted under 35 U.S.C. 154(b) by 106 days.

(21) Appl. No.: 15/810,487

(22) Filed: Nov. 13, 2017

(65) Prior Publication Data

US 2018/0132961 A1 May 17, 2018

Related U.S. Application Data

(60) Provisional application No. 62/422,147, filed on Nov. 15, 2016.

(51) Int. Cl.
*A61B 90/10* (2016.01)
*A61N 1/05* (2006.01)
(Continued)

(52) U.S. Cl.
CPC .......... *A61B 90/10* (2016.02); *A61M 39/0247* (2013.01); *A61N 1/0539* (2013.01);
(Continued)

(58) Field of Classification Search
CPC .......... A61M 25/02; A61M 2025/0213; A61M 2025/024; A61M 2025/0246;
(Continued)

(56) References Cited

U.S. PATENT DOCUMENTS 5,464,446 A 11/1995 Dreesen et al.
5,693,032 A * 12/1997 Bierman ............... A61M 25/02
604/174
(Continued)

FOREIGN PATENT DOCUMENTS

EP 1016432 7/2000
GB 2344054 5/2000

OTHER PUBLICATIONS

Guardian Cranial Burr Hole Cover System, Clinician's Manual, ANS, Apr. 2009.
(Continued)

*Primary Examiner* — Kami A Bosworth
(74) *Attorney, Agent, or Firm* — Mueting, Raasch and Gebhardt, P.A.

(57) ABSTRACT

Techniques, systems and apparatus for anchoring a therapy delivery device within a body portal are disclosed. An anchoring apparatus may comprise a first part comprising an outer sidewall and opposing grip surfaces. The outer sidewall may extend around a longitudinal axis of the apparatus to define an outer perimeter, at least a portion which may engage a surface of the body portal. A second part may comprise first and second activation members and a slot configured to receive the therapy delivery device. When the therapy delivery device is received in the slot and the second part is moved generally along the longitudinal axis, the first and second activation members may move the opposing grip surfaces toward one another to thereby anchor the therapy delivery device between the opposing grip surfaces.

29 Claims, 6 Drawing Sheets

(51) Int. Cl.
*A61M 39/02* (2006.01)
*A61M 25/02* (2006.01)

(52) U.S. Cl.
CPC .. *A61B 2090/103* (2016.02); *A61M 2025/028* (2013.01); *A61M 2039/0261* (2013.01)

(58) Field of Classification Search
CPC .... A61M 2025/028; A61M 2025/0286; A61M 2025/04; A61M 39/0247; A61M 2039/025; A61M 2039/0261; A61M 2039/0273; A61M 2039/0279; A61M 2039/0288; A61B 2090/103; A61B 90/10; A61N 1/0539
See application file for complete search history.

(56) References Cited

U.S. PATENT DOCUMENTS

| | | | |
|---|---|---|---|
| 5,843,150 A | 12/1998 | Dreesen et al. | |
| 5,865,842 A | 2/1999 | Knuth et al. | |
| 5,927,277 A | 7/1999 | Baudino et al. | |
| 5,954,687 A | 9/1999 | Baudino | |
| 6,044,304 A | 3/2000 | Baudino | |
| 6,134,477 A | 10/2000 | Knuteson | |
| 6,210,417 B1 | 4/2001 | Baudino et al. | |
| 6,214,016 B1 | 4/2001 | Williams et al. | |
| 6,267,769 B1 | 7/2001 | Truwit | |
| 6,321,104 B1 | 11/2001 | Gielen et al. | |
| 6,752,812 B1 | 6/2004 | Truwit | |
| 6,902,569 B2 | 6/2005 | Parmer et al. | |
| 7,033,326 B1 | 4/2006 | Pianca et al. | |
| 7,177,701 B1 | 2/2007 | Pianca | |
| 7,204,840 B2 | 4/2007 | Skakoon et al. | |
| 7,235,084 B2 | 6/2007 | Skakoon et al. | |
| 7,346,391 B1 | 3/2008 | Osorio et al. | |
| 7,421,297 B2 | 9/2008 | Giftakis et al. | |
| 7,580,756 B2 | 8/2009 | Schulte et al. | |
| 7,588,581 B2 | 9/2009 | Solar et al. | |
| 7,604,644 B2 | 10/2009 | Schulte et al. | |
| 7,604,655 B2 | 10/2009 | Warnick | |
| 7,637,915 B2 | 12/2009 | Parmer et al. | |
| 7,704,260 B2 | 4/2010 | Skakoon et al. | |
| 7,749,199 B2 | 7/2010 | Mogg | |
| 7,766,394 B2 | 8/2010 | Sage et al. | |
| 7,949,410 B2 | 5/2011 | Rodriguez | |
| 7,981,119 B2 | 7/2011 | Lando et al. | |
| 7,981,120 B2 | 7/2011 | Mazzocchi et al. | |
| 8,007,473 B2 | 8/2011 | Smith et al. | |
| 8,038,685 B2 | 10/2011 | Bedenbaugh | |
| 8,050,772 B1 | 11/2011 | Daglow et al. | |
| 8,315,714 B2 | 11/2012 | Daglow et al. | |
| 8,417,353 B2 | 4/2013 | Appenrodt et al. | |
| 8,425,534 B2 | 4/2013 | Barker | |
| 8,556,860 B2 | 10/2013 | Stratton et al. | |
| 8,603,038 B2 | 12/2013 | Nelson | |
| 8,731,686 B2 | 5/2014 | Lane et al. | |
| 8,738,151 B2 | 5/2014 | Nelson | |
| 8,945,089 B2 | 2/2015 | Johnson et al. | |
| 9,468,751 B2 | 10/2016 | Bonde | |
| 9,474,896 B2 | 10/2016 | Lopez | |
| 9,539,421 B2 | 1/2017 | Bonde et al. | |
| 9,604,052 B2 | 3/2017 | Behymer et al. | |
| 2002/0052610 A1 | 5/2002 | Skakoon et al. | |
| 2005/0075680 A1* | 4/2005 | Lowry | A61N 1/0531 607/45 |
| 2005/0182420 A1 | 8/2005 | Schulte et al. | |
| 2005/0182421 A1 | 8/2005 | Schulte et al. | |
| 2005/0182422 A1 | 8/2005 | Schulte et al. | |
| 2005/0182423 A1 | 8/2005 | Schulte et al. | |
| 2005/0182424 A1 | 8/2005 | Schulte et al. | |
| 2005/0182425 A1 | 8/2005 | Schulte et al. | |
| 2005/0182464 A1 | 8/2005 | Schulte et al. | |
| 2005/0192594 A1 | 9/2005 | Skakoon et al. | |
| 2007/0249980 A1 | 10/2007 | Carrez et al. | |
| 2008/0017206 A1 | 1/2008 | Becker et al. | |
| 2008/0172068 A1 | 7/2008 | Adams et al. | |
| 2009/0112327 A1 | 4/2009 | Lane et al. | |
| 2009/0118804 A1 | 5/2009 | Moffitt et al. | |
| 2010/0268308 A1* | 10/2010 | Rossby | A61M 39/0247 607/116 |
| 2012/0209206 A1* | 8/2012 | Scandone, Jr. | A61M 25/04 604/175 |
| 2012/0316628 A1* | 12/2012 | Lopez | A61N 1/0539 607/116 |
| 2013/0018319 A1* | 1/2013 | Abe | A61M 25/02 604/174 |
| 2013/0066410 A1* | 3/2013 | Funderburk | A61N 1/0539 607/116 |
| 2014/0257325 A1 | 9/2014 | Chavez et al. | |
| 2015/0148747 A1* | 5/2015 | Whitley | A61M 39/1011 604/180 |
| 2016/0361529 A1* | 12/2016 | Finch, Jr. | A61M 39/0247 |

OTHER PUBLICATIONS

LJ.S. Provisional Patent Application, U.S. Appl. No. 62/400,140, filed Sep. 27, 2016.
LJ.S. Provisional Patent Application, U.S. Appl. No. 62/446,923, filed Jan. 17, 2017.

* cited by examiner

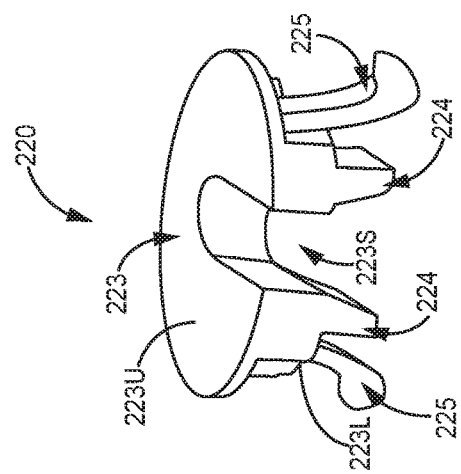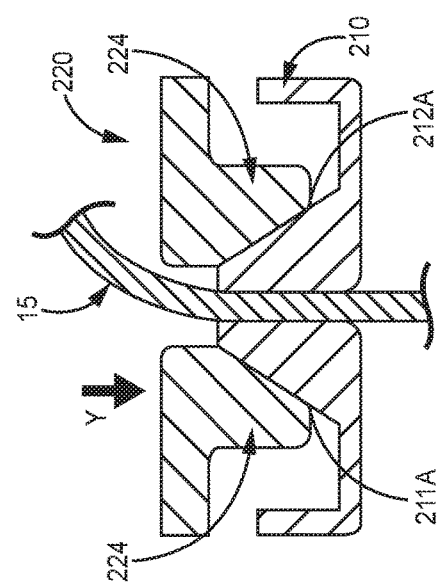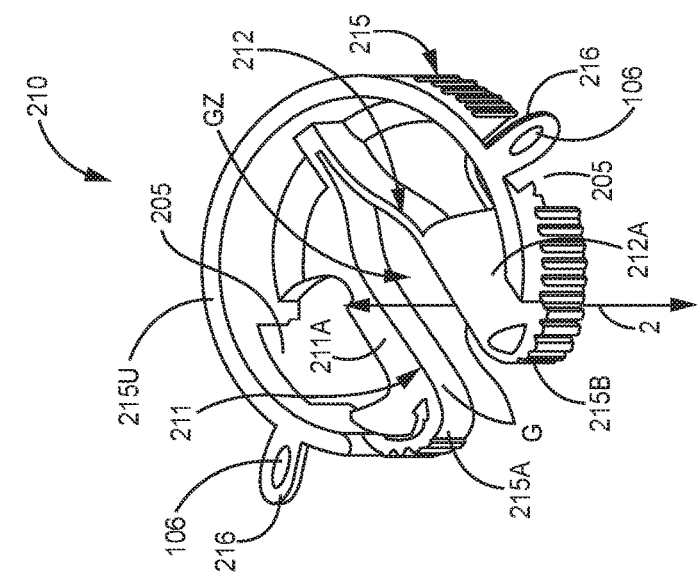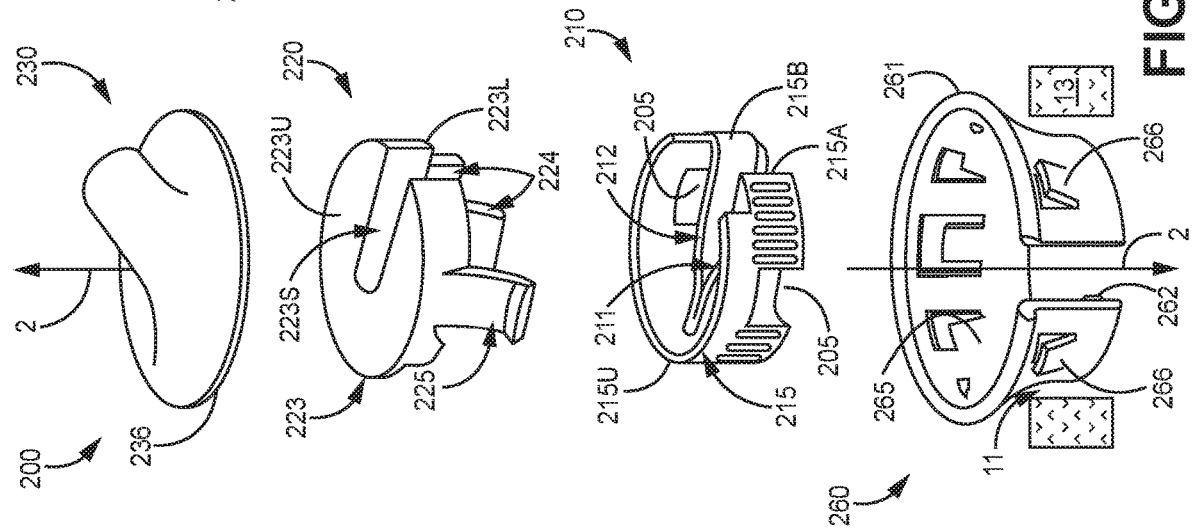

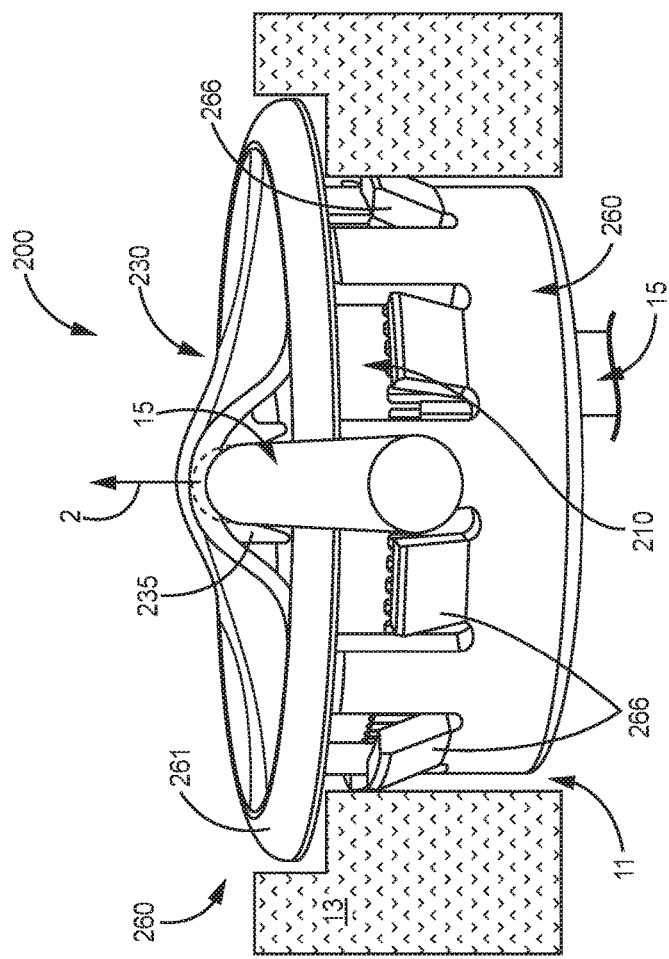
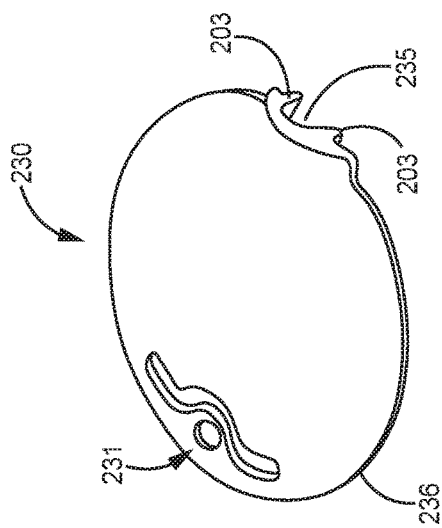
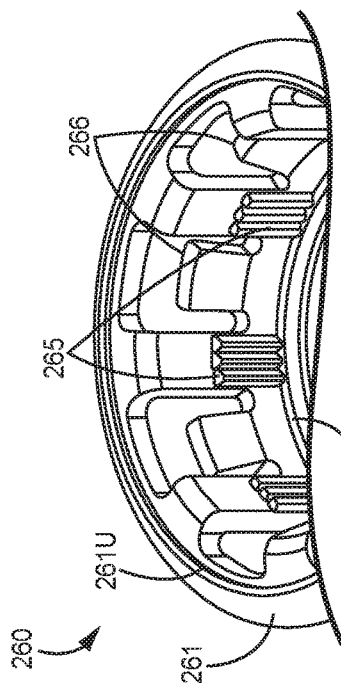
FIG. 3A
FIG. 3B
FIG. 3C

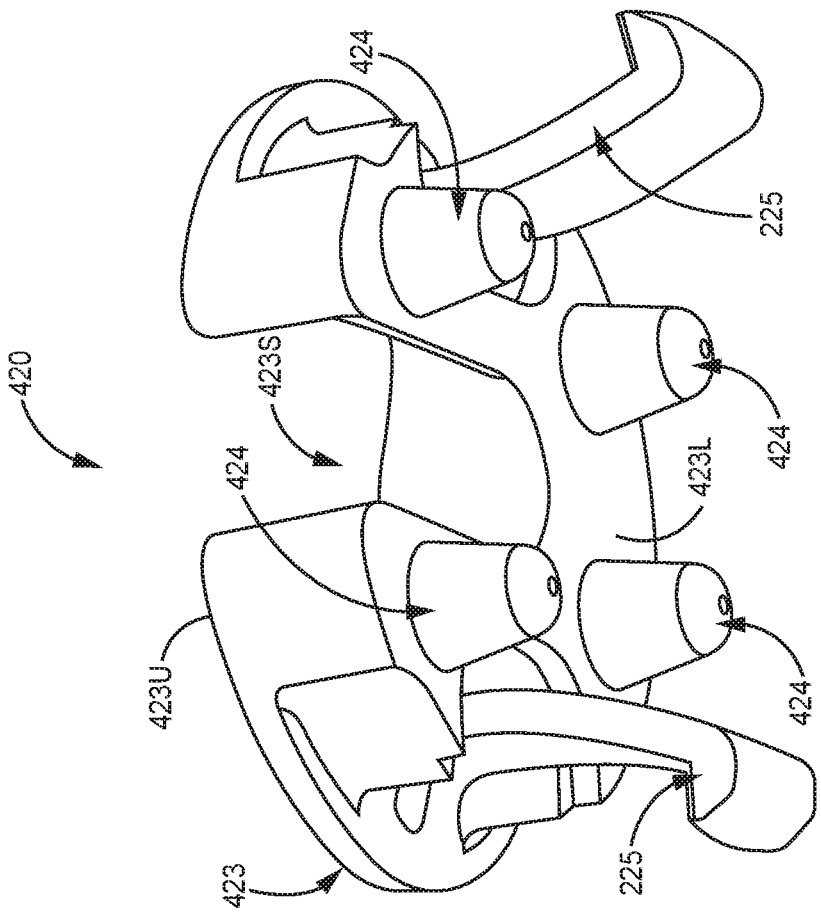
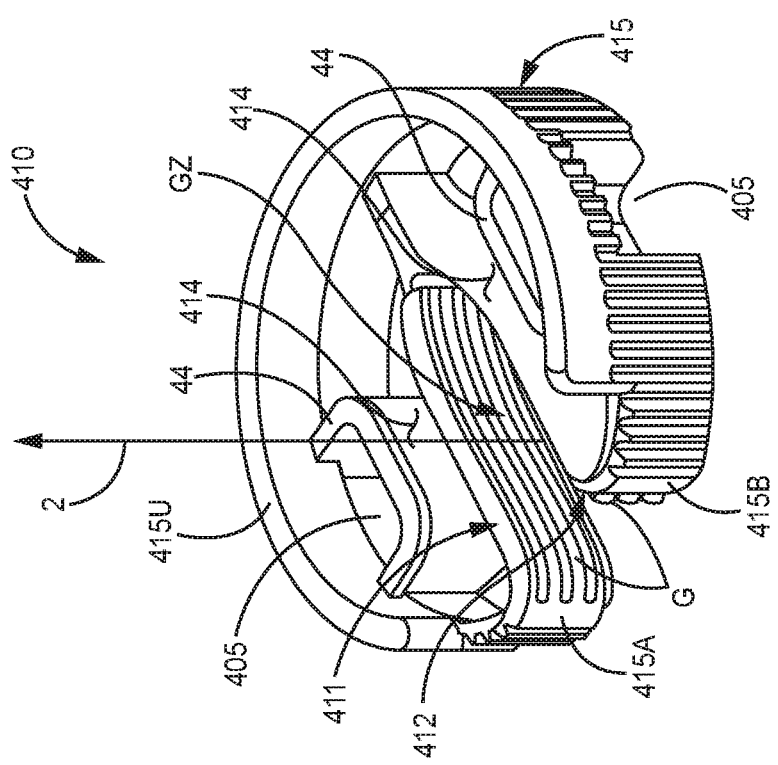
FIG. 4A
FIG. 4B

MEDICAL DEVICE ANCHORING

PRIORITY CLAIM

This application claims priority to U.S. Provisional Application having the same title, the Ser. No. 62/437,863, which was filed on Nov. 15, 2016, and is hereby incorporated by reference in its entirety.

TECHNICAL FIELD

The present disclosure pertains to medical devices and more particularly to anchoring an elongate portion of the medical device within a body portal, for example, a burr hole formed in a skull or cranium of a patient.

SUMMARY

An apparatus for anchoring a therapy delivery device within a body portal is disclosed. The therapy delivery device may comprise a medical electrical lead, a catheter, a stimulation device, or any other device that is adapted to be anchored within a body portal. The apparatus may comprise a first part and a second part. The first part may comprise an outer sidewall and opposing grip surfaces. In one embodiment, the outer sidewall may extend around a longitudinal axis of the apparatus to define an outer perimeter. The outer sidewall may have ends and the grip surfaces may extend inward from the ends of the outer sidewall. In one example, the grip surfaces are formed by first and second inner sidewall folding inward from the ends of the outer sidewall.

In one example, at least a portion of the outer sidewall is configured to engage a surface of the body portal, the opposing grip surfaces may face toward the longitudinal axis and be configured to receive the therapy delivery device therebetween.

The apparatus may further comprise a second part comprising a lower surface, first and second activation members protruding from the lower surface, and a slot configured to receive the therapy delivery device. A first activation member may be located on one side of the slot and the second activation member may be located on the other side of the slot. In one embodiment, when the therapy delivery device is received in the slot and the second part is moved generally along the longitudinal axis, the first and second activation members move the opposing grip surfaces toward one another to thereby anchor the therapy delivery device between the opposing grip surfaces.

According to other aspects, at least one of the first and second activation members comprises multiple activation members. For instance, multiple activation members (e.g., two such members) may be located on either side of the slot. In one case, the first part may comprise a respective activation surface for each of the opposing grip surfaces and each of the first and second activation members may be configured to come in confronting engagement with a respective one of the activation surfaces to move the opposing grip surfaces toward one another. In some examples, each activation surface may extend at an angle relative to the respective grip surface and each of the first and second activation members may comprise an angled flange.

In some examples, the first part may comprise incompressible filler and each of the first and second activation members may be configured to displace a respective portion of the filler. The incompressible filler may extend within the outer sidewall, and the first and second activation member may comprise a stud configured to displace the respective portion of the filler.

As another example, the apparatus may comprise a base ring configured to be seated within the body portal, the base ring comprising a rim. The outer sidewall of the first part may be configured to seat on the rim of the base ring. The base ring may be configured to be seated within the body portal, and the base ring may comprise a sidewall configured to engage the outer sidewall of the first part. The sidewall of the base ring may comprise interlocking features and the outer sidewall of the first part includes an outer perimeter surface formed with a plurality of engagement features being equally spaced apart from one another around the outer perimeter of the first part and being configured to mate with the interlocking features of the base ring. The base ring may comprise at least one locking feature configured to engage a surface of the body portal.

The apparatus may, in some cases, comprise a cover that may be configured to fit over the first part. The cover may comprise a channel configured to receive the therapy delivery device. The channel of the cover may comprise opposing lips configured to grip a portion of the therapy delivery device. A base ring may be configured to be seated in the body portal and may comprise an upper rim configured to engage a perimeter edge of the cover.

In another embodiment, a medical system is disclosed that comprises an implantable medical device, a therapy delivery device configured to be coupled to the implantable medical device and an apparatus configured to anchor a portion of the therapy delivery device within a body portal. The implantable medical device may be a stimulation device configured to deliver electrical, ultrasonic, magnetic, optical, or any other type of stimulation to provide therapy to patients suffering from a variety of conditions, such as chronic pain, tremor, Parkinson's disease, epilepsy, OCD, depression, dystonia, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Alternatively, the implantable medical device may be a pump or other fluid delivery devices. Example fluid delivery devices may be used for chronic delivery of therapeutic agents, such as drugs. Typically, such devices provide therapy continuously or periodically according to parameters contained within a program.

The therapy delivery device may be a device for coupling to the implantable medical device for delivering therapy to the patient. For instance, it may be a medical electrical lead, a device for delivering optical stimulation (e.g., and that comprises an optical channel), or a combination thereof. It may be a catheter for delivering a therapeutic agent to the patient. In some examples, the therapy delivery device may be mechanically coupled to the implantable medical device, and in other examples, the therapy delivery device may be functionally but not mechanically coupled to the implantable medical device. For example, the therapy delivery device may be adapted to send and/or receive wireless electrical or other signals from the implantable medical device.

The apparatus of the medical system may comprise a first part comprising an outer sidewall extending around a longitudinal axis of the apparatus to define an outer perimeter, at least a portion of which is configured to engage a surface of the body portal. The first part may further comprise first and second inner sidewalls extending alongside one another within the outer sidewall. The first and second inner sidewalls may be spaced apart to receive the therapy delivery device therebetween.

The apparatus may further comprise a second part comprising a lower surface, first and second activation members protruding from the lower surface, and a slot configured to receive the therapy delivery device. The first activation member may be located on one side of the slot and the second activation may be located on the other side of the slot.

The second part may be configured to be moved generally along the longitudinal axis toward the first part to thereby cause the first and second activation members to move the first and second inner sidewalls toward one another. The first and second inner sidewalls may thereby anchor the therapy delivery device therebetween when the therapy delivery device is received in the slot of the second part.

According to some examples, each of the first and second inner sidewalls may further comprise an activation surface facing generally away from the longitudinal axis and each of the first and second activation members may comprise an angled flange configured to come into confronting engagement with a respective one of the activation surfaces. The first part may, in some cases, further comprise filler extending within the outer sidewall, the filler being configured to be displaced to thereby move the first and second inner sidewalls towards one another. Each of the first and second activation members may comprise a portion configured to displace the filler of the first part to thereby move the first and second inner sidewalls towards one another. The outer sidewall may comprise first and second apertures and the second part may further comprise first and second detent legs, each configured to extend through a corresponding one of the first and second apertures to engage a surface of the body portal.

The apparatus of the medical system may further comprise a base ring comprising a sidewall configured to form a perimeter surface of the body portal when the apparatus is fitted within the body portal. The outer sidewall of the first part may be configured to contact the sidewall of the base ring. The base ring may comprise a lower rim and the outer sidewall of the first part may be configured to be seated on the lower rim. The sidewall of the base ring may comprise at least one locking feature that extends away from the longitudinal axis and that is configured to engage with a surface of the body portal. The base ring and outer sidewall of the first part may be configured to engage with one another to prevent significant rotation of the first part relative to the second part around the longitudinal axis of the apparatus.

The apparatus may comprise a cover that is configured to be positioned over an upper surface of the second part. The cover may comprise a channel configured to receive the therapy delivery device. The apparatus may further comprise a base ring configured to be seated within the body portal, the base ring may comprise a rim configured to engage a perimeter edge of the cover. The channel of the cover may comprise opposing lips configured to grip the therapy delivery device.

In another example, an apparatus for anchoring a therapy delivery device within a body portal is disclosed. The apparatus may comprise first means comprising sidewall means, gripping means, and aperture means. The sidewall means may be for engaging a surface of the body portal, and the gripping means may be for receiving the therapy delivery device and for moving perpendicular to a longitudinal axis. The apparatus may further comprise second means comprising slot means, activation means, and leg means. The slot means may be for receiving the therapy delivery device, the activation means may be for causing the gripping means to move substantially perpendicular to the longitudinal axis to grip the therapy delivery device, and the leg means may be for extending through the aperture means to engage a surface of the body portal. The second means may be for moving generally along the longitudinal axis towards the first means whereby said activation means moves substantially perpendicular to the longitudinal axis to grip the therapy delivery device and the leg means extends through the aperture means to engage a surface of the body portal.

BRIEF DESCRIPTION OF THE DRAWINGS

The following drawings are illustrative of particular embodiments and do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 2A is a perspective view of an anchoring apparatus, according to some embodiments; the apparatus being exploded along a longitudinal axis thereof;

FIGS. 2B-C are perspective views of a first part and a second part, respectively, of the apparatus, according to some embodiments;

FIG. 2D is a schematic cross-section view of the first and second parts, according to some embodiments;

FIG. 3A is a perspective view of the apparatus, according to some embodiments, being fitted in a burr hole of a cranium that is shown in partial cross-section;

FIG. 3B is a perspective view of a portion of a base ring of the apparatus, according to some embodiments;

FIG. 3C is a perspective view of a cover of the apparatus, according to some embodiments;

FIGS. 4A-B are perspective views of first and second parts, respectively, which may be employed in lieu of the first and second parts of FIGS. 2A-D and 3A, in an alternate embodiment of the apparatus.

DETAILED DESCRIPTION

The following detailed description is exemplary in nature and is not intended to limit the scope, applicability, or configuration of embodiments disclosed herein. Rather, the description provides practical examples, of which those skilled in the art will recognize suitable alternatives. Examples of constructions, materials, dimensions and fabrication processes are provided for select elements and all other elements employ that which is known by those skilled in the art. Embodiments of anchoring apparatus, disclosed herein, are suitable for mounting/fixing in or over a body portal, for example, a cranial burr hole, in order to anchor in place an elongate portion of a medical device, such as an electrical lead or a catheter.

Example anchoring apparatus as disclosed herein may be employed in medical procedures for treating a variety of neurological conditions. Treating such medical conditions, including but not limited to, Parkinson's disease, essential tremor and dystonia, require access to the brain, typically through a burr hole formed in the skull or cranium, for the insertion of deep brain stimulating electrodes. Burr holes may also be formed for the insertion of a delivery catheter, for example, to provide drug therapy for similar conditions, or an extraction catheter, for example, a hydrocephalus shunt. Stereotactic apparatus and procedures, which are known to those skilled in the art, may be employed by surgeons to locate inserted electrodes and/or drug delivery ports in target regions of the brain. While these examples are illustrative, other body portals may receive therapy delivery devices that may be anchored therein using techniques of the current disclosure.

Figure 1A:
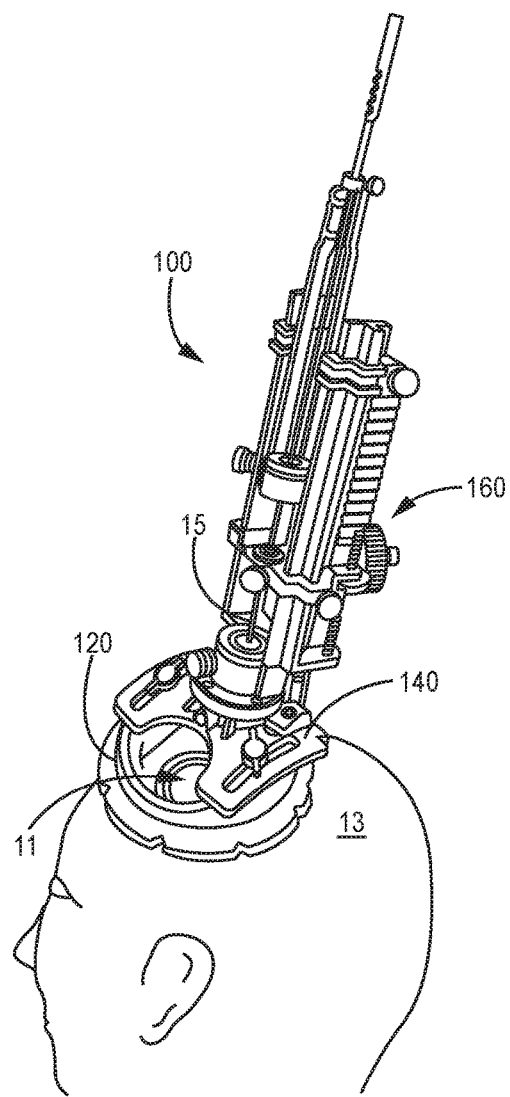
FIG. 1A is a schematic showing an exemplary stereotactic guidance system mounted to a patient's cranium.

FIG. 1A is a perspective view of an exemplary stereotactic guidance system 100 (e.g. Medtronic Nexdrive® Micropositioning Drive attached to the Medtronic Nexframe® system) mounted to a patient's skull or cranium 13. FIG. 1A illustrates a ring 120 of guidance system 100, which extends around a perimeter of a body portal, or burr hole 11 formed in cranium 13, supporting a socket assembly 140 to which a micropositioning drive 160 is attached. An anchoring mechanism 112 (FIG. 1B; e.g. the Medtronic StimLoc® base) may be mounted around burr hole 11 and fastened to cranium 13, for example, via screws received through holes 106 in a base ring of mechanism 112, prior to attaching ring 120 of guidance system 100. FIG. 1A further illustrates a therapy delivery device 15 (e.g., an elongate therapy delivery lead or catheter) of a medical system being held within drive 160 for advancement through burr hole 11 and into the cranial space for positioning on a target region of the brain.

Figure 1B:
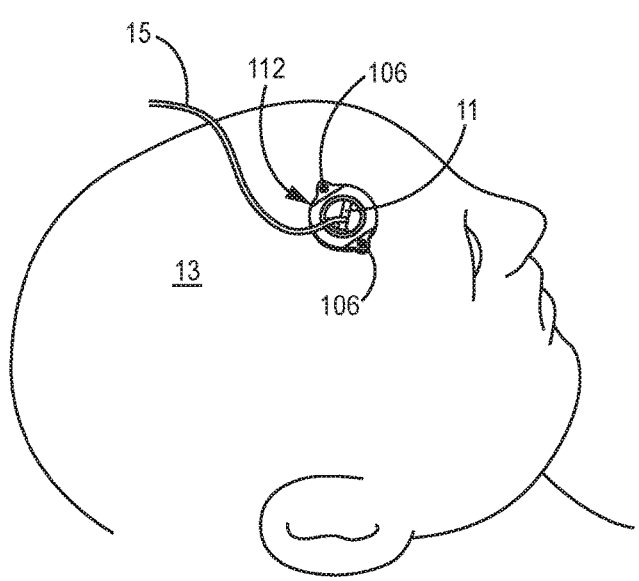
FIG. 1B is a schematic showing an elongate portion of an implantable medical device extending through an anchoring mechanism after the guidance system has been removed.
Figure 1C:
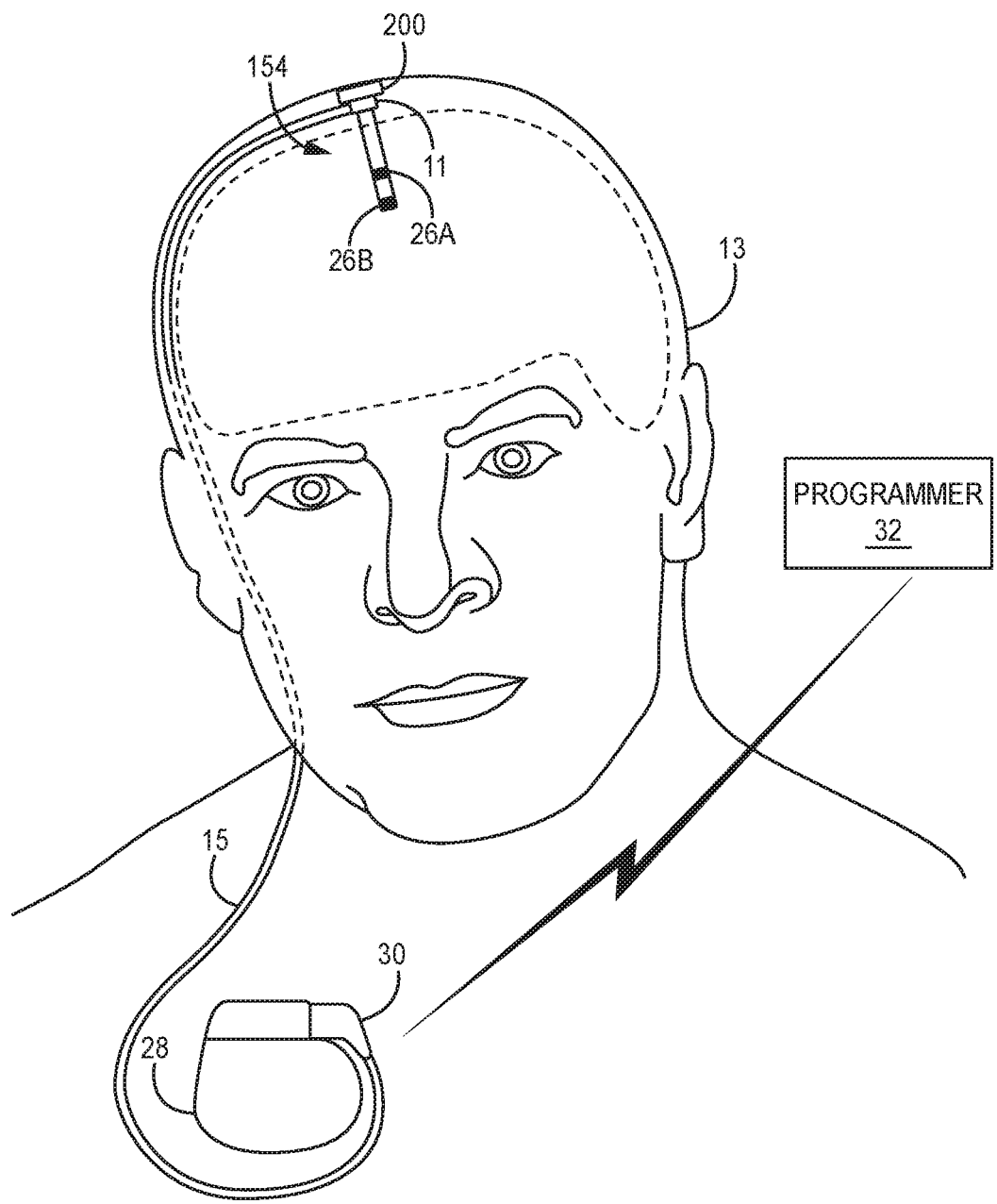
FIG. 1C is a schematic showing an example implantable medical therapy system.

FIG. 1B illustrates therapy delivery device 15 after guidance system 100 has been removed. FIG. 1B further illustrates therapy delivery device 15 extending through a slot of mechanism 112 to be anchored between mechanism 112 and a cover or a cap that snaps into place thereover (not shown; e.g., the Medtronic StimLoc® base). Those skilled in the art appreciate that a proximal length of therapy delivery device 15, outside the cranial space, may be routed, beneath the scalp and subcutaneously, to a therapy generator of the device, for example, an implantable medical device 28 shown in the schematic of FIG. 1C, which is implanted subcutaneously in proximity to the patient's clavicle. With further reference to FIG. 1C, a distal length 154 of therapy delivery device 15, which has been advanced through burr hole 11, is shown including therapy delivery ports or electrodes 26A, 26B positioned at the target region of the brain. In some cases, therapy delivery device 15 may comprise a lead extension. For example, a proximal end of lead extension may be coupled to implantable medical device 28, and a distal end of lead extension may be coupled to a proximal end of lead. The distal end of lead may be received by burr hole 11.

FIG. 1C is a schematic showing an implanted medical therapy system, according to some embodiments of the present disclosure, in which embodiments of an anchoring apparatus 200, which are described below, may be employed. FIG. 1C illustrates the system including the aforementioned implantable medical device 28, which may comprise a stimulation engine to deliver stimulation therapy. FIG. 1C further illustrates therapy delivery device 15, which is shown as a therapy delivery lead in this example, coupled thereto via a connector 30 that terminates the proximal length thereof. FIG. 1C further illustrates distal length 154 of therapy delivery device 15 extending through apparatus 200, which is fastened to the patient's cranium 13 around the above-described burr hole 11. According to embodiments described below, apparatus 200 is configured to secure therapy delivery device 15 in place so that electrodes 26A, 26B remain positioned at the aforementioned target regions of the patient's brain for stimulation thereof over the course of the system implant.

According to an exemplary embodiment, implantable medical device 28 is configured to deliver electrical stimulation therapy to, and/or sense electrical signals from the patient's brain, via lead electrodes 26A, 26B that are mounted to distal length 154 of therapy delivery device 15 and electrically coupled to connector 30 via insulated conductors. Those skilled in the art are familiar with suitable configurations and constructions for therapy delivery device 15 and implantable medical device 28. Implantable medical device 28 may include processing circuitry, memory, signal generation circuitry, sensing circuitry, telemetry circuitry, and a power source. In some cases, implantable medical device 28 may comprise a pump or other mechanisms for delivering a therapeutic agent to the patient.

The memory of implantable medical device 28 may include computer-readable instructions that are executed by the processing circuitry, for example, to deliver stimulation therapy to the patient, sense physiological signals of the patient, and/or perform other functions related to treating one or more conditions of the patient. The telemetry circuitry may include any suitable hardware, firmware, software or any combination thereof for communicating with another device, such as a programmer 32. Under the control of the processing circuitry the telemetry circuitry may receive downlink telemetry from and send uplink telemetry to programmer 32 with the aid of an antenna, which may be internal and/or external. Programmer 32 may be a handheld computing device, computer workstation, or networked computing device that includes electronics and other internal components necessary or desirable for executing the functions associated with the system.

Turning now to a discussion of anchoring mechanisms, FIG. 2A is a perspective view of apparatus 200 (exploded along a longitudinal axis 2 thereof) that anchors the aforementioned therapy delivery device 15 within a body portal, for example, the aforementioned burr hole 11 formed through the patient's cranium 13 (FIGS. 1A-C). FIG. 2A illustrates apparatus 200 including a first part 210, a second part 220, and a base ring 260, which, according to some embodiments, forms a perimeter surface 265 of the portal/burr hole 11, when ring 260 is fitted therein, so that an outer perimeter of first part 210, for example, being defined by an outer sidewall 215 thereof, engages perimeter surface 265 when fitted within the portal/burr hole 11, for example, being seated on a lower inner rim 262 of ring 260 (better seen in FIG. 3B). Outer sidewall 215 is shown extending around longitudinal axis 2 from a first end 215A thereof to a second end 215B thereof, and first and second ends 215A, 215B being spaced apart from one another to allow an operator to place first part 210 in burr hole 11 and around therapy delivery device 15, which already extends through burr hole 11. FIG. 2A further illustrates first part 210 including first and second inner sidewalls 211, 212 folding inward from respective first and second ends 215A, 215B of outer sidewall 215, and extending alongside one another within outer sidewall 215. With reference to the perspective view of first part 210, shown in FIG. 2B, each of inner sidewalls 211, 212 includes a grip surface G facing toward axis 2, wherein grip surfaces G are spaced apart from one another to define a grip zone GZ therebetween. With further reference to FIG. 2A, second part 220 of apparatus 200 is shown including a disk-like member 223 that has an open slot 223S formed therethrough from an upper surface 223U thereof to a lower surface 223L thereof, so that when first and second parts 210, 220 are assembled together in apparatus 200, lower surface 223L extends adjacent to an upper surface 215U of first part outer sidewall 215, and slot 223S is aligned with grip zone GZ of first part 210. According to the illustrated embodiment, slot 223S and grip zone GZ are each sized to receive passage of therapy delivery device 15 therethrough, and, when second part 220 is moved longitudinally against first part 210, activation members 224 of second part 220, which extend from disk-like member lower surface 223L, move grip surfaces G of first part inner sidewalls 211, 212 toward one another to anchor therapy delivery device 15 therebetween. In some cases, this movement of the grip surfaces may be substantially perpendicular to the longitudinal axis.

With further reference to FIG. 2B, in conjunction with the perspective view of second part 220 in FIG. 2C, according to some embodiments, each inner sidewall 211, 212 of first part 210 includes an activation surface 211A, 212A located and oriented for confronting engagement of an angled flange of a corresponding activation member 224 of second part 220 therewith, when second part 220 is moved longitudinally (along longitudinal axis 2) against first part 210, for example, per arrow Y shown in the schematic cross-section of FIG. 2D. Each activation surface 211A, 212A of first part 210 is shown being located opposite the corresponding grip surface G, facing generally away from axis 2, and extending at an angle relative to the corresponding grip surface G, so that the confronting engagement of the angled flanges of second part activation members 224 pushes grip surfaces G together to anchor therapy delivery device 15, for example, as shown in the schematic section of FIG. 2D. To enhance the anchoring, grip surfaces G may be formed by texturing and/or overlaying inner sidewalls 211, 212 with a relatively tacky medical grade polymer, such as silicone rubber. Grip surfaces may be moved generally perpendicular to the longitudinal axis 2.

FIGS. 2A and 2C further illustrate second part 220 of apparatus 200 including first and second detent legs 225 that protrude from lower surface 223L of disk-like member 223, being located opposite one another on either side of slot 223S. According to the illustrated embodiment, when second part lower surface 223L extends adjacent to first part upper surface 215U, and slot 223S is aligned with first part grip zone GZ, each leg 225 extends through a corresponding aperture 205 of first part outer sidewall 215 to engage the perimeter surface of body portal/burr hole 11, for example, by interlocking with lower inner rim 262 of base ring 260. The interlock of one of legs 225 with lower inner rim 262 is illustrated for an alternate embodiment of apparatus 200 in FIG. 4D.

FIG. 2A further illustrates apparatus 200 including a cover 230, which is sized to fit over an entirety of upper surface 223U of second part disk-like member 223, according to some embodiments, for example, as illustrated in the perspective view of FIG. 3A. FIG. 3A illustrates cover 230 engaged with base ring 260, when first part 210 is seated on lower inner rim 262 of ring 260, and second part 220 has been moved against first part 210 to anchor therapy delivery device 15 between grip surfaces G of first part 210, and to interlock detent legs 225 with lower inner rim 262 of ring 260. Thus, the engagement of cover 230 and detent legs 225 with base ring 260 serve to secure the anchoring of therapy delivery device 15 between grip surfaces G of first part inner sidewalls 211, 212. According to some embodiments, and with reference to FIG. 3B, base ring upper outer rim 261 may include an undercut 261U to engage a perimeter edge 236 of cover 230. FIG. 3A further illustrates cover 230 including a channel 235 sized to receive a length of the anchored therapy delivery device 15; and FIG. 3C illustrates an opening of channel 235, which is located at a perimeter edge 236 of cover 230, having opposing lips 203 to grip the length of anchored therapy delivery device 15 therebetween. FIG. 3C further illustrates cover 230 including a removal feature 231, for example, formed by a hole and corresponding cut-out relief formed through cover 230, which facilitates engagement of a tool with cover 230 to unlock perimeter edge 236 of cover 230 from undercut 261U of base ring upper outer rim 261.

With further reference to FIG. 2A, in conjunction with FIGS. 3A-B, a sidewall of base ring 260, which extends between upper outer rim 261 and lower inner rim 262, includes locking features 266 formed therein. FIGS. 2A and 3A-B illustrate locking features 266 extending outward, away from longitudinal axis 2, and being configured to engage with cranium 13, within a perimeter of burr hole 11, when upper outer rim 216 rests on an outer surface of cranium 13, which is shown in partial cross-section in FIG. 3A. Although FIG. 2A shows base ring 260 including a slot, alternate embodiments need not include the slot. With further reference to FIGS. 2A-B, an outer perimeter surface of first part outer sidewall 215 is formed with a plurality of uniform engagement features, for example, outward protruding ridges, which are equally spaced apart from one another around the perimeter of first part 210, and are configured to mate with uniform interlocking features, for example, inward protruding ridges, formed along perimeter surface 265 of base ring 260 (FIG. 3B). This mating of first part outer sidewall 215 with perimeter surface 265 of base ring 260 can prevent significant rotation of first part 210 relative to base ring 260, around longitudinal axis 2, and an operator can seat first part 210 in a plurality of orientations about longitudinal axis 2 of apparatus 200 (e.g., in 5 degree increments), for example, to accommodate various trajectories of implanted therapy delivery device 15 through burr hole 11.

With further reference to FIG. 3A, in some embodiments, apparatus 200 is adapted to sit entirely, or substantially entirely, within burr hole 11, without extending above the surface of the portion of cranium 13 surrounding burr hole 11, thereby minimizing a profile of apparatus 200. Furthermore, a longitudinal extent of grip surfaces may approach a thickness of cranium 13 (e.g., about 5 mm) at burr hole 11, for example, greater than 50% of the cranium thickness, to maximize a gripping force between grip surfaces G.

According to some alternate embodiments, base ring 260 is not included in apparatus 200 so that outer sidewall 215 of first part 210 interfaces directly with cranium 13 when first part 210 is inserted within burr hole 11. FIG. 2B illustrates first part 210 including optional mounting members 216 extending from upper surface 215U of outer sidewall 215 to rest on a surface of cranium 13 surrounding burr hole 11, when first part 210 is inserted therein. Each mounting member 216 is shown including the aforementioned screw hole 106 to receive a screw for fastening first part 210 to the cranium, and mounting members 216 may be relatively flexible to conform to a curvature of the cranium when first part 210 is fastened.

According to exemplary embodiments of apparatus 200, cover 230, first part 210, second part 220, and base ring 260 may each be formed from any suitably elastic and rigid medical grade material, either metal (e.g., titanium or stainless steel), or plastic, (e.g., polyether ether ketone—PEEK, or polysulfone), or a combination thereof. As was mentioned above, grip surfaces G may be formed in part by an overlay of medical grade silicone rubber on inner sidewalls 211, 212.

FIGS. 4A-B are perspective views of first and second parts 410, 420, respectively, which may be included in anchoring apparatus 200, in lieu of the above described first and second parts 210, 220, according to some alternate embodiments. FIG. 4A illustrates first part 410 including an outer sidewall 415, and first and second inner sidewalls 411, 412, wherein inner sidewalls 411, 412 fold inward from respective first and second ends 415A, 415B of outer sidewall 415, and extend alongside one another within outer sidewall 415. Like inner sidewalls 211, 212 of first part 210, each inner sidewall 411, 412 of first part 410 includes a grip surface G facing toward axis 2, wherein grip surfaces G are spaced apart from one another to define a grip zone GZ therebetween. To enhance the anchoring, grip surfaces G may be formed by texturing and/or overlaying inner sidewalls 411, 412 with a relatively tacky medical grade polymer, such as silicone rubber. FIG. 4A further illustrates first part 410 including a relatively soft and incompressible filler 414 (e.g., having a durometer <5 on a shore A scale) extending within outer sidewall 415 and alongside inner sidewalls 411, 412, on either side of grip zone GZ. Filler 414 may be a medical grade silicone rubber, and outer and inner sidewalls 415, 411, 412 may be formed from one or more of any of the aforementioned suitably elastic and rigid medical grade materials. FIG. 4B illustrates second part 420 including a disk-like member 423 and activation members 424 that protrude from a lower surface 423L thereof, wherein each member 424 may be formed as a rounded stud. An open slot 423S is shown being formed through disk-like member 423 from an upper surface 423U thereof to lower surface 423L thereof, wherein activation members 424 are located on either side of slit 423S. FIG. 4B further illustrates second part 420 including detent legs 225 like second part 220, and with reference back to FIG. 4A, first part sidewall 415 includes apertures 405 formed therethrough, wherein each aperture 405 is sized to allow an extension of a corresponding detent leg 225 therethrough. In FIG. 4A, a barrier wall 44 is shown extending between each aperture 405 and filler 414, on either side of inner sidewalls 411, 412, to contain filler 414 in first part 410.

Figure 4C:
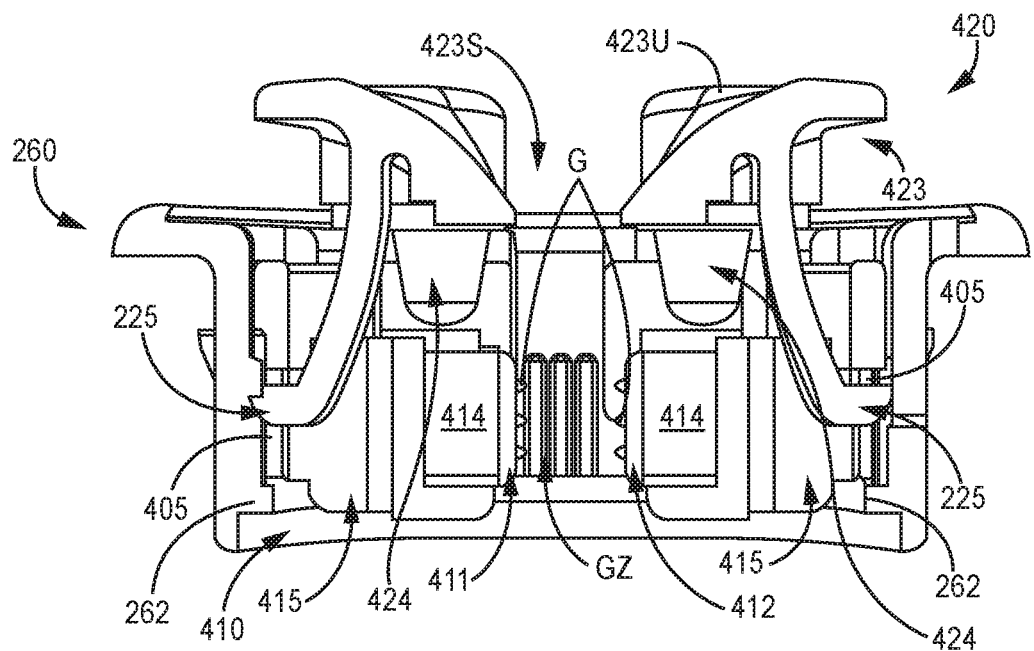
FIGS. 4C-D are cross-section views of the apparatus including the first and second parts of FIGS. 4A-B, according to some embodiments.
Figure 4D:
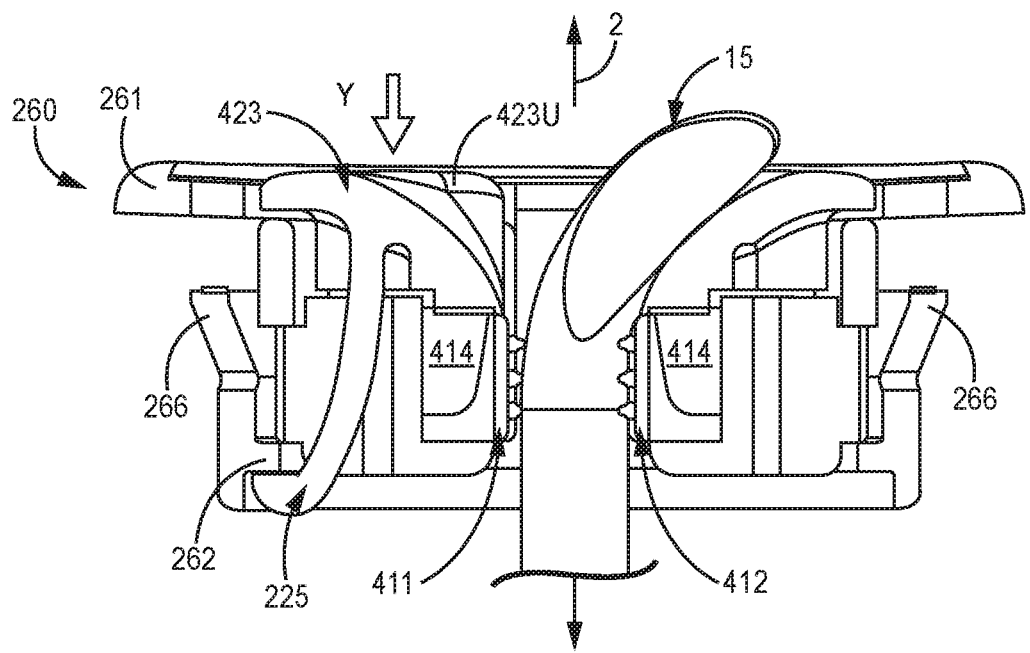

According to the illustrated example, when first and second parts 410, 420 are assembled together in apparatus 200 (in lieu of parts 210, 220), lower surface 423L of second part disk-like member 423 extends adjacent to an upper surface 415U of first part outer sidewall 415, and slot 423S is aligned with grip zone GZ, for example, as illustrated in the cross-section views of FIGS. 4C-D. FIG. 4C shows outer sidewall 415 of first part 410 seated on inner lower rim 262 of base ring 260, and each detent leg 225 extending through the corresponding aperture 405, so that each activation members 424 of second part 420 is positioned just above first part filler 414. With reference back to FIG. 4A, note that an outer perimeter surface of outer sidewall 415 of first part 410 may be configured in a manner similar to first part 210 so that the outer perimeter surface of outer sidewall 415 will engage with perimeter surface 265 formed by ring 260, as described above for first part 210. FIG. 4D shows second part 420 having been moved longitudinally (along longitudinal axis 2) against first part 410, per arrow Y, so that each detent leg 225 interlocks with lower inner rim 262 of base ring 260, and activation members 424 are in confronting engagement with filler 414. According to the illustrated embodiment, the confronting engagement displaces filler 414 to move grip surfaces G of inner sidewalls 411, 412 toward one another so that grip zone GZ of first part 410 anchors therapy delivery device 15. Although not shown, cover 230 may be fitted over an entirety of upper surface 423U of second part disk-like member 423, being engaged with base ring 260 as described above in conjunction with FIGS. 3A-C, so that the length of the anchored therapy delivery device 15 extends through cover channel 235. FIGS. 4B-D further illustrate upper surface 423U having a smoothed and uniform contour around slot 423S to provide strain relief for the length of anchored therapy delivery device 15. Such a contour may also be employed in second part 210.

The foregoing detailed description sets forth exemplary embodiments, of which various features may be mixed and matched to form a number of addition embodiments that are not outside the scope of the instant disclosure. Furthermore, it may be appreciated that various modifications and changes can be made without departing from the scope and spirit of the disclosure as set forth in the appended claims.

What is claimed is:

1. An apparatus for anchoring a therapy delivery device within a cranial burr hole formed in a cranium, comprising:
   a first part comprising an outer sidewall and opposing grip surfaces, the outer sidewall extending around a longitudinal axis of the apparatus to define an outer perimeter, at least a portion of the outer sidewall being configured to interface with the cranium, the opposing grip surfaces facing toward the longitudinal axis and being configured to receive the therapy delivery device therebetween; and
   a second part comprising a lower surface, first and second activation members protruding from the lower surface, and a slot configured to receive the therapy delivery device, wherein the first activation member is located on one side of the slot and the second activation member is located on another side of the slot;
   wherein, when the therapy delivery device is received in the slot and the second part is moved generally along the longitudinal axis, the first and second activation members move the opposing grip surfaces toward one another to thereby anchor the therapy delivery device between the opposing grip surfaces.

2. The apparatus of claim 1, wherein the second part comprises two additional activation members.

3. The apparatus of claim 1, wherein the first part further comprises, a respective activation surface for each of the opposing grip surfaces, and wherein each of the first and second activation members is configured to come in confronting engagement with a respective one of the activation surfaces to move the opposing grip surfaces toward one another.

4. The apparatus of claim 3, wherein each activation surface extends at an angle relative to the respective grip surface and each of the first and second activation members comprises an angled flange.

5. The apparatus of claim 1, wherein the first part further comprises incompressible filler and wherein each of the first and second activation members is configured to displace a respective portion of the filler.

6. The apparatus of claim 5, wherein the incompressible filler extends within the outer sidewall, and each of the first and second activation members comprises a stud configured to displace the respective portion of the filler.

7. The apparatus of claim 1, further comprising a cover configured to fit over the first part, the cover including a channel configured to receive the therapy delivery device.

8. The apparatus of claim 7, wherein the channel of the cover comprises opposing lips configured to grip a portion of the therapy delivery device.

9. A medical system comprising:
an implantable medical device;
a therapy delivery device configured to be coupled to the implantable medical device; and
an apparatus configured to anchor a portion of the therapy delivery device within a cranial burr hole formed in a cranium, comprising:
a first part comprising an outer sidewall extending around a longitudinal axis of the apparatus to define an outer perimeter, at least a portion of which is configured to interface with the cranium, the first part further comprising first and second inner sidewalls extending alongside one another within the outer sidewall, the first and second inner sidewalls being spaced apart to receive the therapy delivery device therebetween; and
a second part comprising a lower surface, first and second activation members protruding from the lower surface, and a slot configured to receive the therapy delivery device, wherein the first activation member is located on one side of the slot and the second activation member is located on another side of the slot; and
wherein the second part is configured to be moved generally along the longitudinal axis toward the first part to thereby cause the first and second activation members to move the first and second inner sidewalls toward one another, the first and second inner sidewalls thereby anchoring the therapy delivery device therebetween when the therapy delivery device is received in the slot of the second part.

10. The medical system of claim 9, wherein each of the first and second inner sidewalls further comprises an activation surface facing generally away from the longitudinal axis and each of the first and second activation members comprises an angled flange configured to come into confronting engagement with a respective one of the activation surfaces.

11. The medical system of claim 9, wherein the first part further comprises filler extending within the outer sidewall, the filler being configured to be displaced to thereby move the first and second inner sidewalls towards one another.

12. The medical system of claim 11, wherein each of the first and second activation members comprises a portion configured to displace the filler of the first part to thereby move the first and second inner sidewalls towards one another.

13. The medical system of claim 9, wherein the outer sidewall comprises first and second apertures and wherein the second part further comprises first and second detent legs, each detent leg configured to extend through a corresponding one of the first and second apertures to engage a surface of the cranium.

14. The medical system of claim 9, wherein the apparatus further comprises a cover being configured to be positioned over an upper surface of the second part, the cover comprising a channel configured to receive the therapy delivery device.

15. The medical system of claim 14, wherein the channel of the cover comprises opposing lips configured to grip the therapy delivery device.

16. An apparatus for anchoring a therapy delivery device within a body portal, comprising:
a base ring configured to be seated within the body portal and comprising a sidewall;
a first part comprising an outer sidewall and opposing grip surfaces, the outer sidewall extending around a longitudinal axis of the apparatus to define an outer perimeter, the opposing grip surfaces facing toward the longitudinal axis and being configured to receive the therapy delivery device therebetween, wherein the outer sidewall of the first part is configured to engage the sidewall of the base ring;
a second part comprising a lower surface, first and second activation members protruding from the lower surface, and a slot configured to receive the therapy delivery device, wherein the first activation member is located on one side of the slot and the second activation member is located on another side of the slot; and
wherein, when the therapy delivery device is received in the slot and the second part is moved generally along the longitudinal axis, the first and second activation members move the opposing grip surfaces toward one another to thereby anchor the therapy delivery device between the opposing grip surfaces.

17. The apparatus of claim 16, wherein the base ring further comprises a rim, wherein the outer sidewall of the first part is configured to engage the sidewall of the base ring by being seated on the rim of the base ring.

18. The apparatus of claim 16, wherein the base ring further comprises at least one locking feature configured to engage a surface of the body portal.

19. The apparatus of claim 16, further comprising a cover configured to fit over the first part, the cover including a channel configured to receive the therapy delivery device.

20. The apparatus of claim 19, wherein the base ring comprises an upper rim configured to engage a perimeter edge of the cover.

21. The apparatus of claim 19, wherein the channel of the cover comprises opposing lips configured to grip a portion of the therapy delivery device.

22. The apparatus of claim 16, wherein the sidewall of the base ring comprises interlocking features and the outer sidewall of the first part comprises an outer perimeter surface formed with a plurality of engagement features being equally spaced apart from one another around the outer perimeter of the first part and being configured to mate with the interlocking features of the base ring.

23. A medical system comprising:
an implantable medical device;
a therapy delivery device configured to be coupled to the implantable medical device; and
an apparatus configured to anchor a portion of the therapy delivery device within a body portal, comprising:
a base ring comprising a sidewall configured to form a perimeter surface of the body portal when the apparatus is fitted within the body portal;
a first part comprising an outer sidewall extending around a longitudinal axis of the apparatus to define an outer perimeter, the outer sidewall of the first part configured to contact the sidewall of the base ring, the first part further comprising first and second inner sidewalls extending alongside one another within the outer sidewall, the first and second inner sidewalls being spaced apart to receive the therapy delivery device therebetween; and
a second part comprising a lower surface, first and second activation members protruding from the lower surface, and a slot configured to receive the therapy delivery device, wherein the first activation member is located on one side of the slot and the second activation member is located on another side of the slot; and wherein the second part is configured to be moved generally along the longitudinal axis toward the first part to thereby cause the first and second activation members to move the first and second inner sidewalls toward one another, the first and second inner sidewalls thereby anchoring the therapy delivery device therebetween when the therapy delivery device is received in the slot of the second part.

24. The medical system of claim 23, wherein the base ring comprises a lower rim and wherein the outer sidewall of the first part is configured to be seated on the lower rim.

25. The medical system of claim 23, wherein the sidewall of the base ring comprises at least one locking feature that extends away from the longitudinal axis, and wherein the at least one locking feature is configured to engage with a surface of the body portal.

26. The medical system of claim 23, wherein the base ring and the outer sidewall of the first part are configured to engage with one another to prevent significant rotation of the first part relative to the second part around the longitudinal axis of the apparatus.

27. The medical system of claim 23, wherein the apparatus further comprises a cover being configured to be positioned over an upper surface of the second part, the cover comprising a channel configured to receive the therapy delivery device.

28. The medical system of claim 27, wherein the base ring comprises an upper rim configured to engage a perimeter edge of the cover.

29. The medical system of claim 27, wherein the channel of the cover comprises opposing lips configured to grip the therapy delivery device.

* * * * *